US012588910B1

(12) United States Patent
Berrada-Sounni et al.

(10) Patent No.: US 12,588,910 B1
(45) Date of Patent: Mar. 31, 2026

(54) VASCULAR FLOW RESTRICTION DEVICES AND RELATED SYSTEMS AND METHODS

(71) Applicant: VahatiCor, Inc., Los Gatos, CA (US)

(72) Inventors: Marwan Berrada-Sounni, Los Gatos, CA (US); Kevin H. Van Bladel, Livermore, CA (US); Benjamin M. Trapp, Scottsdale, AZ (US)

(73) Assignee: Vahaticor, Inc., Santa Clara, CA (US)

( * ) Notice: Subject to any disclaimer, the term of this patent is extended or adjusted under 35 U.S.C. 154(b) by 415 days.

(21) Appl. No.: 17/982,912

(22) Filed: Nov. 8, 2022

Related U.S. Application Data

(60) Provisional application No. 63/277,057, filed on Nov. 8, 2021.

(51) Int. Cl.
*A61B 17/12* (2006.01)

(52) U.S. Cl.
CPC .. *A61B 17/12036* (2013.01); *A61B 17/12109* (2013.01); *A61B 17/12168* (2013.01); *A61B 2017/12054* (2013.01)

(58) Field of Classification Search
CPC ........ A61B 17/12036; A61B 17/12109; A61B 17/12168; A61B 2017/12054
See application file for complete search history.

(56) References Cited

U.S. PATENT DOCUMENTS

| | | | |
|---|---|---|---|
| 6,953,476 B1 | 10/2005 | Shalev | |
| 7,442,204 B2 | 10/2008 | Schwammenthal et al. | |

| | | | |
|---|---|---|---|
| 8,439,963 B2 | 5/2013 | Dickinson et al. | |
| 8,764,772 B2 | 7/2014 | Tekulve | |
| 8,764,813 B2 | 7/2014 | Jantzen et al. | |
| 8,858,612 B2 | 10/2014 | Ben-Muvhar et al. | |
| 8,911,489 B2 | 12/2014 | Ben-Muvhar | |
| 9,364,354 B2 | 6/2016 | Ben-Muvhar et al. | |
| 9,597,204 B2 | 3/2017 | Benary et al. | |
| 9,744,059 B2 | 8/2017 | Ben-Muvhar | |
| 10,022,128 B2 | 7/2018 | Bodewadt et al. | |
| 10,368,981 B2 | 8/2019 | Nitzan | |
| 10,398,443 B2 | 9/2019 | Bodewadt et al. | |
| 10,973,527 B2 | 4/2021 | Deshmukh et al. | |
| 11,039,915 B2 | 6/2021 | Tuval et al. | |
| 2003/0040772 A1* | 2/2003 | Hyodoh ..................... A61F 2/90 |
| | | | 606/200 |

(Continued)

FOREIGN PATENT DOCUMENTS

| | | | |
|---|---|---|---|
| CA | 3072236 A1 | 4/2019 | |
| EP | 2959864 A1 | 12/2015 | |

(Continued)

OTHER PUBLICATIONS

Verheye, Stefan et al., Efficacy of a Device to Narrow the Coronary Sinus in Refractory Angina; The New England Journal of Medicine, 372;6; Feb. 5, 2015; pp. 519-527.

*Primary Examiner* — Erin McGrath
(74) *Attorney, Agent, or Firm* — Downs Rachlin Martin PLLC

(57) ABSTRACT

System and method for deploying a flow restriction device in patient vascular and recapturing and repositioning the flow device after full or partial deployment. Disclosed systems and methods permit confirmation of device placement, such as by measuring a pressure drop across the partially or fully deployed device in the coronary sinus before release of the device and permanent implantation.

1 Claim, 4 Drawing Sheets

Fully Deployed

10

11

'Cinched'

(56)                    References Cited

U.S. PATENT DOCUMENTS

| | | |
|---|---|---|
| 2003/0070676 A1 | 4/2003 | Cooper et al. |
| 2003/0097172 A1 | 5/2003 | Shalev |
| 2005/0267567 A1 | 12/2005 | Shalev |
| 2006/0030920 A1 | 2/2006 | Ben-Muvhar |
| 2006/0106449 A1 | 5/2006 | Ben Muvhar |
| 2007/0027525 A1 | 2/2007 | Ben-Muvhar |
| 2009/0054723 A1* | 2/2009 | Khairkhahan ... A61B 17/12122 |
| | | 600/16 |
| 2010/0106178 A1 | 4/2010 | Obermiller |
| 2010/0179643 A1 | 7/2010 | Shalev |
| 2011/0112625 A1 | 5/2011 | Ben-Muvhar et al. |
| 2013/0178750 A1 | 7/2013 | Sheehan et al. |
| 2013/0317593 A1 | 11/2013 | Ben-Muvhar et al. |
| 2017/0333227 A1 | 11/2017 | Ben-Muvhar |
| 2017/0340434 A1 | 11/2017 | Cerchiari et al. |
| 2019/0262118 A1 | 8/2019 | Eigler et al. |
| 2020/0155331 A1 | 5/2020 | Ben-Muvhar et al. |
| 2020/0229956 A1 | 7/2020 | Jackson et al. |
| 2020/0237495 A1 | 7/2020 | Jackson et al. |
| 2020/0368053 A1 | 11/2020 | Ben-Muvhar et al. |
| 2020/0375721 A1 | 12/2020 | Celermajer et al. |
| 2021/0077256 A1 | 3/2021 | Pellegrini et al. |
| 2021/0290358 A1 | 9/2021 | Goodman et al. |
| 2021/0338990 A1 | 11/2021 | Eigler et al. |
| 2022/0287831 A1* | 9/2022 | Thornton .................. A61F 2/90 |
| 2022/0387009 A1* | 12/2022 | Bukhdruker ....... A61B 17/0057 |

FOREIGN PATENT DOCUMENTS

| | | |
|---|---|---|
| EP | 3300672 A1 | 4/2018 |
| WO | 200172239 A2 | 10/2001 |
| WO | 2003028522 A2 | 4/2003 |
| WO | 2020214416 A1 | 10/2020 |
| WO | 2021007289 A1 | 1/2021 |
| WO | 2021226014 A2 | 11/2021 |

* cited by examiner

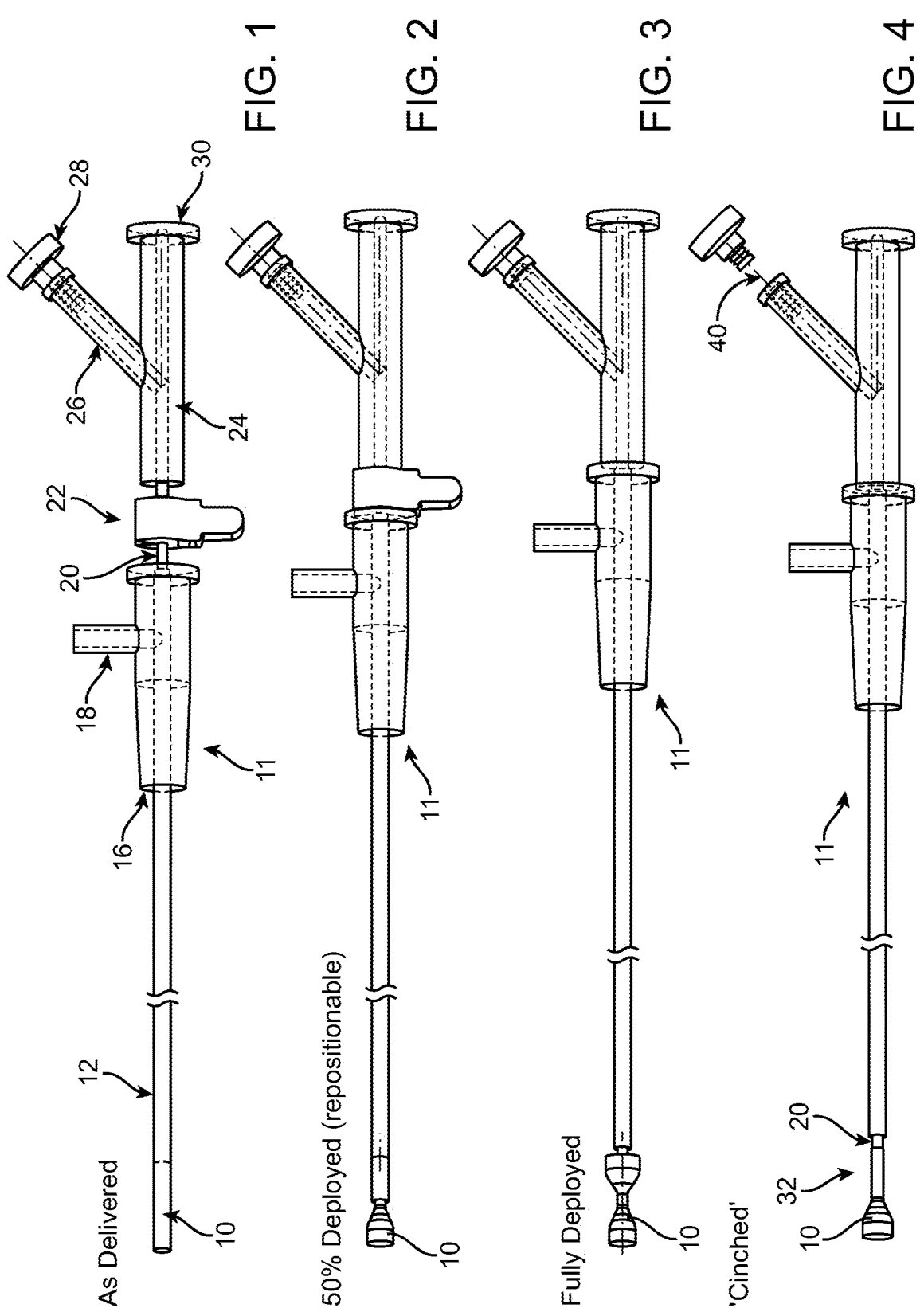

VASCULAR FLOW RESTRICTION DEVICES AND RELATED SYSTEMS AND METHODS

RELATED APPLICATION DATA

This application claims the benefit of priority of U.S. Provisional Patent Application Ser. No. 63/277,057, filed Nov. 8, 2021, and titled "Vascular Flow Restriction Devices and Related Systems and Methods", which is incorporated by reference herein in its entirety.

FIELD OF THE DISCLOSURE

The present disclosure generally relates to vascular flow control for therapeutic effect, and more specifically to vascular flow restriction devices and related systems and methods, in particular devices configured as coronary sinus reducers.

BACKGROUND

Vascular flow restrictive devices such as coronary sinus reducers direct flow through a smaller "throat" section to achieve a pressure drop of therapeutic benefit. While the general configuration of such devices is well-established, existing devices can present a number of drawbacks. For example, existing devices generally are not readily retrievable after deployment in the event that the flow restriction does not provide a pressure drop sufficient for a desired therapeutic effect.

Another drawback of many existing devices arises from the common structure of devices as formed from a non-occlusive stainless steel or nitinol mesh structure. A drawback with this conventional design is that the pressure drop is not immediate and is generated only (when and if) the device endothelializes and uses the body tissue as an impermeable barrier to blood flow.

A further potential issue with such prior mesh devices can arise when stagnation of blood flow in the 'trapped' area between the device and the vessel causes thrombus to form, but the device has not yet been rendered occlusive (through endothelialization). This may lead to a potential of thrombus release into the circulation with risk of stroke or pulmonary embolism.

SUMMARY OF DISCLOSURE

In one implementation, the present disclosure is directed to a delivery system for a vascular flow restriction device. The system includes an inner catheter having a distal end configured for insertion into a patient's vasculature and an opposite proximal end, the distal end further configured to receive a collapsed flow restriction device over a distal end thereof; a retractable outer sheath disposed over the inner catheter, the outer sheath having proximal and distal ends; and a recapture fiber extending through at least one of the inner catheter or outer sheath, the recapture fiber manipulable at the proximal end of the inner catheter and configured to engage a flow restriction device disposed at the proximal end of the inner catheter, wherein manipulation of the recapture fiber at the proximal end controls expansion or collapse of the flow restriction device.

In another implementation, the present disclosure is directed to a delivery system for a vascular flow restriction device. The system includes an inner catheter with a distal end configured for insertion into a patient's vasculature and a proximal end with an inner catheter hub, the inner catheter defining at least one lumen having a side opening on the inner catheter proximally spaced from the distal end; a retractable outer sheath disposed over the inner catheter, the outer sheath having a distal end configured for insertion into the patient's vasculature and a proximal end with an outer sheath hub, wherein relative movement of the outer sheath hub and inner catheter hub exposes or covers the distal end of the inner catheter; an expandable flow restriction device received on the distal end of the inner catheter distally with respect to the side opening and inside the outer sheath, wherein the flow restriction device comprises a self-expanding structure with two open ends; and a recapture fiber extending from the inner catheter hub through the inner catheter lumen and out the side opening to engage the expandable flow restriction device, the recapture fiber manipulable at the inner catheter hub to control expansion or collapse of the flow restriction device.

In yet another implementation, the present disclosure is directed to a method for delivering a vascular flow restriction device. The method includes positioning a distal end of a delivery device at a treatment location in a patient's vasculature, wherein the delivery device includes a vascular flow restriction device disposed at the distal end; partially deploying the flow restriction device from the delivery device at the treatment location; performing a procedure to confirm placement of the partially deployed flow restriction device; fully deploying the flow restriction device, detaching the flow restriction device from the delivery device and removing the delivery device when placement is confirmed; and recapturing the partially deployed flow restriction device on to the delivery device when placement is not confirmed.

BRIEF DESCRIPTION OF DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein:

FIG. 1 is a schematic side view of a coronary sinus reducer deployment system according to an embodiment of the present disclosure.

FIG. 2 is a schematic side view of the coronary sinus reducer system shown in FIG. 1, depicted in a 50% deployed state.

FIG. 3 is a schematic side view of the coronary sinus reducer system shown in FIG. 1, depicted in a fully deployed state.

FIG. 4 a schematic side view of the coronary sinus reducer system shown in FIG. 1, depicted with the reducer device in a cinched state.

DETAILED DESCRIPTION

Figure 5:
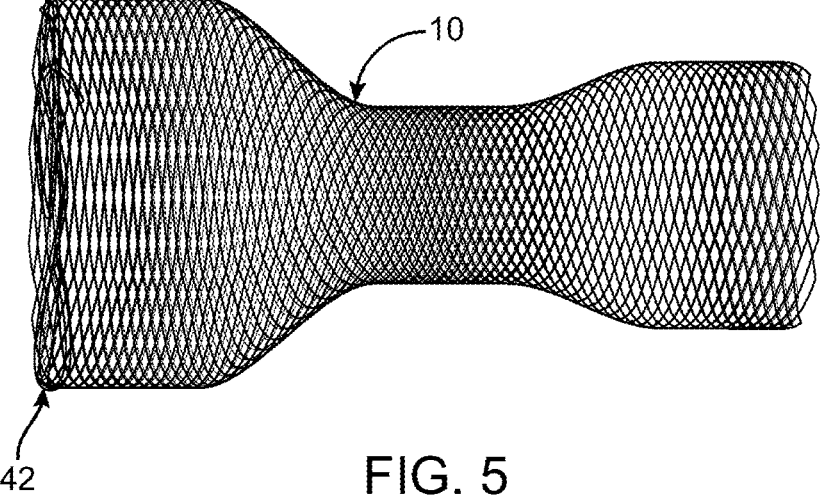
FIG. 5 is a side view of an embodiment of a coronary sinus reducer according to an embodiment of the present disclosure.
Figure 6:
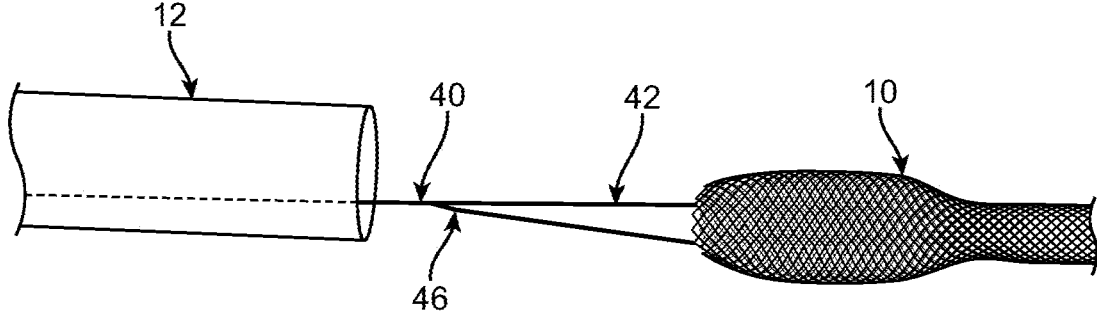
FIG. 6 is a side view of a deployment system outer sheath, coronary sinus reducer and recapture fiber according to an alternative embodiment of the present disclosure.

Exemplary embodiments of vascular flow restriction device 10 are shown in FIG. 1-8. Embodiments of vascular flow restriction device 10 shown in FIGS. 5-8 are shown as a bare wire mesh device. While in some embodiments device 10 may be used in this form, in more preferred embodiments, the wire mesh has a covering as described herein below with reference to FIG. 9 and device 100. Further alternative full or partial coatings or coverings are described in Applicant's pending International Application No. PCT/US2021/030556, filed May 4, 2021, which is incorporated herein in its entirety.

As shown in FIGS. 1-4, in one illustrative embodiment, delivery system 11 for vascular flow restriction device 10 includes inner catheter 20 on which restriction device 10 is disposed and covered by outer sheath 12 during delivery. Relative motion between inner catheter 20 and outer sheath 12 is controlled proximally by inner catheter hub 24 and outer sheath hub 16, respectively. 50% deployment stop 22 is used as described further below to ensure that deployment of restriction device 10 does not pass 50% deployment until position or other deployment criteria are confirmed. Other components of delivery system 11 may include flush port 18 on outer sheath hub 16 and guidewire port 30 on inner catheter hub 24. Additionally, inner catheter hub 24 includes recapture fiber (side) port 26 through which recapture fiber 40 passes and is controlled by recapture knob 28 as further described below.

Using conventional interventional cardiology/catheterization techniques and procedures, the distal end of delivery system 11 is positioned at the desired location treatment location within the patient's vasculature. For placement in the coronary sinus, the distal end of delivery system 11 is positioned within the coronary sinus past the branch of the posterior interventricular vein and before the left posterior vein branch. This position will prevent occlusion of the side branches and good placement of the flow restriction. The delivery system outer sheath 12 can slide back to expose the flow restriction device 10, which is located on the distal end of inner catheter 20. The flow restriction device 10 may be constructed as a self-expanding wire mesh, for example made of Nitinol, and thus will self-expand as the outer sheath 12 is retracted back. Radiopaque markers, such as platinum-filled wires or other suitable markers, may be incorporated into or disposed into the mesh structure to facilitate visualization.

With the outer sheath 12 withdrawn approximately half way, i.e. the 50% position, the middle part of the flow restriction device 10 is exposed and radiopaque dye can be injected to determine if the flow restriction device 10 is in an appropriate position and adequately conforming to the vessel wall. The flow restriction device 10 could, at this point in the procedure, be retrieved and advanced further into the vessel for better contact with the vessel wall. If the evaluation of flow restriction device placement is assessed as appropriate, the outer sheath 12 is retracted further to expose the remainder of the hourglass shape of the flow restriction device 10. Again, the second half of the flow restriction device can be evaluated for proper contact with the vessel wall and position within the coronary sinus. At this point, the pressure differential can be measured to ensure an adequate therapeutic effect will be generated.

As shown in FIGS. 5-8, with the recapture fiber 40 attached to drawstring 42 on flow restriction device 10, the flow restriction device can still be retrieved into the outer sheath 12 by retracting the recapture fiber 40 to collapse the proximal end onto inner catheter 20 and advancing the outer sheath 12 over the restriction device 10. After the pressure differential is observed and both ends of the restriction device are in appropriate contact with the vessel walls at the confirmed position, one end of the recapture fiber 40 from the side port 26 can be removed which will release the restriction device at that location within the coronary sinus.

In some embodiments, recapture fiber 40 runs down the entire length inside outer sheath 12 from recapture fiber port 26, is threaded through drawstring 42, then runs all the way back through outer sheath 12 to recapture fiber port 26—forming a loop with a bight end 46 through drawstring 42 and with both ends together at recapture port 26 at the proximal end of the inner catheter hub. With this arrangement, pulling on both ends of recapture fiber 40 together causes drawstring 42 to be pulled and thus the end of device 10 is cinched, as shown, for example, in FIG. 6. Once proper placement and effectiveness of device 10 is confirmed, for example by pressure readings, pulling one end of recapture fiber 40 removes the fiber and disconnects flow restriction device 10 from the delivery system. In other embodiments, recapture fiber 40 may be fitted with a releasable clasp at its distal end operable to release or recapture the restriction device drawstring 42.

In terms of positioning in the venous system, the vessel gets larger at the exit point into the right atrium and the blood flow goes from the smaller size to the larger opening. The 50% deployment stop 22 allows the user to deploy the restriction device 10 to the half-way deployed position as shown, for example, in FIG. 2. At the 50% stop, conformity of the distal end of restriction device 10 with the vessel wall can be evaluated to determine if it is in the best location before deploying the second half of the device. A further deployment option is illustrated in FIG. 4 wherein device 10 is deployed, but the proximal end still cinched closed at 32 by recapture fiber 40.

In a further embodiment, using conventional interventional cardiology/catheterization techniques and procedures, the coronary sinus is accessed with a guidewire and guiding catheter (not shown) and fluoroscopic images are taken to gather relevant vessel sizing information. A flow restriction device 10 or 100 as described herein is selected in a size configuration that is slightly oversized (e.g. the ends of the device are approximately 10-60% larger) relative to the native anatomy to ensure sufficient device vessel apposition and that the restriction device will not migrate after deployment. The guiding catheter is then removed and the delivery system 11 is loaded over the guidewire and advanced into the patient. The distal end of the delivery system 11 is positioned at the desired implant location, and outer sheath 12 is retracted until the 50% deployment stop 22 (a removable mechanical stop) is reached. This results in deployment of the distal end of flow restriction device 10. The device location can be checked to ensure it is in the correct location. The device can be withdrawn back into a collapsed configuration by re-advancing outer sheath 12 forward and slight adjustments in position can be made if necessary.

In some embodiments, at the clinician interface of delivery system 11, the outer sheath 12 is designed to be able to be retracted over the inner catheter 20 by a distance corresponding to at least the length of the device 10. Sliding the outer sheath 12 backwards thus allows for full deployment of the flow restriction device 10 while still positioned on inner catheter 20, as shown, for example, in FIG. 7. Alternatively, in cases where it is desirable to assess the positioning of the flow restriction device during delivery, a mechanical stop (e.g. 50% deployment stop 22) is fitted between the outer sheath 12 and the inner catheter 20 that prevents the outer sheath from being fully retracted. This mechanical stop is removeable and when the clinician accepts proper placement, the mechanical stop is removed and full retraction of the outer sheath can be made resulting in full deployment of the device.

Once the positioning is determined to be correct, the 50% deployment stop 22 is removed and outer sheath 12 can be retracted fully. At this point, the device 10 will be fully deployed in the vessel, but the delivery system will remain attached to flow restriction device 10 via recapture fiber 40. At this point, the final location is confirmed and if necessary, pressure readings can be taken to ensure adequate restriction is provided. For example, the distal 'upstream' pressure can be read by removing the guidewire and reading the pressure through the guidewire lumen of the delivery catheter. If necessary, the device can be fully recaptured by unscrewing recapture knob 28 and pulling recapture fiber 40 until the drawstring 42 collapses the proximal end of the flow restriction device 10 and the outer sheath 12 can be re-advanced over the device 10 and the procedure can be repeated. When finished, one end of the recapture fiber 40 is cut and the entire fiber is withdrawn from the system leaving flow restriction device 10 permanently implanted.

Figure 7:
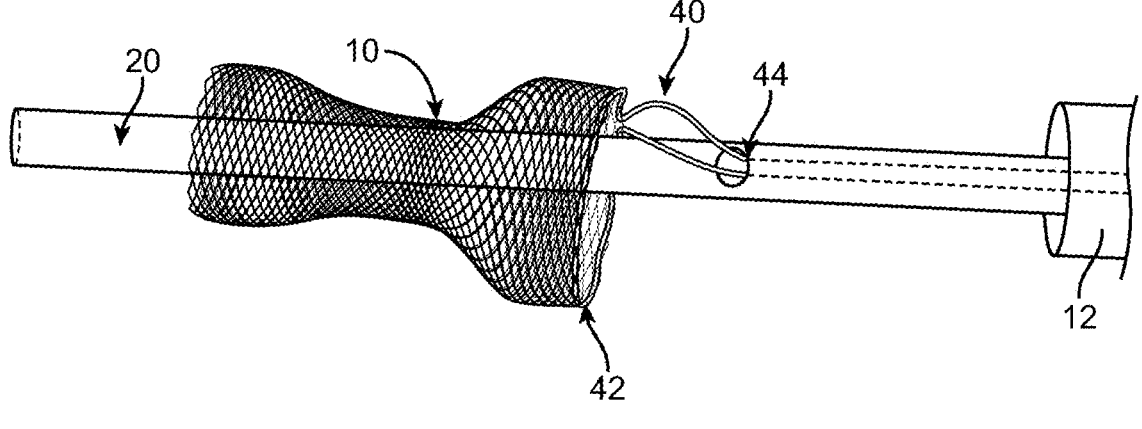
FIG. 7 is side view of a coronary sinus reducer disposed on an inner catheter of a deployment system according to an alternative embodiment of the present disclosure.
Figure 8:
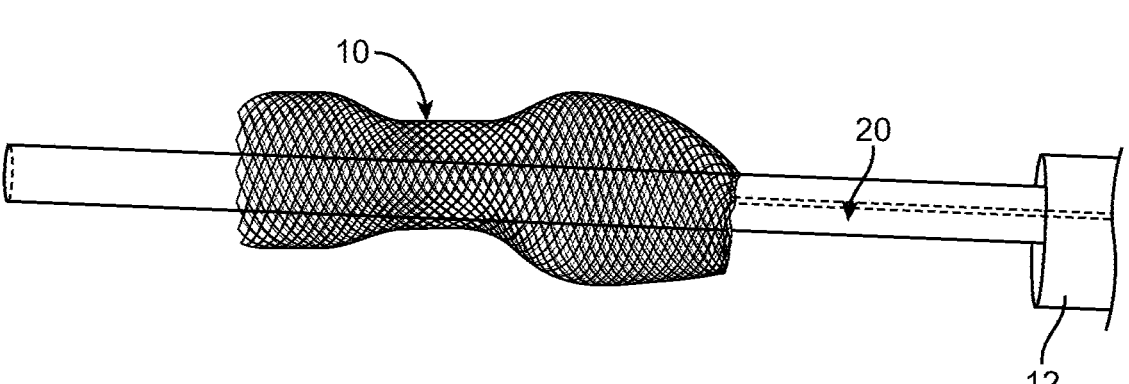
FIG. 8 is a side view of the coronary sinus reducer shown in FIG. 7 in the cinched state.

Using an arrangement as illustrated in FIGS. 7 and 8, placement and effect of the fully deployed restriction device 10 may be confirmed while still traversed by inner catheter 20. If re-deployment is determined to be necessary, device 10 can be cinched down over inner catheter 20. Providing recapture fiber exit port 44 just proximal to the position of restriction device 10 on inner catheter 20 may facilitate cinching and recapture by providing increased control of the cinching and recapture maneuver.

Embodiments of vascular flow restriction devices disclosed herein provide the advantage of allowing full deployment and pressure readings before the restriction device is released from the recapture fiber of the delivery system. The physician or other operator may thus fully deploy restriction device 10, read the pressure, then decide whether to recapture and reposition or complete removal may be needed (e.g. if no pressure drop was created because the patient's anatomy had collaterals that make them not a suitable candidate). Pressure readings may be taken at the distal tip of the delivery catheter (which would be upstream of the vascular flow restriction device). To read pressure at the distal tip, in one embodiment, the guidewire is removed, the guidewire lumen flushed and a pressure gauge configured at the guidewire port communicating with the fluid-filled guidewire lumen. Alternatively, a pressure wire can be inserted into the guidewire port to measure the pressure distally to the restrictor. In a further alternative, a discrete pressure sensor may be fixed at the distal tip of the delivery catheter system.

Figure 9:
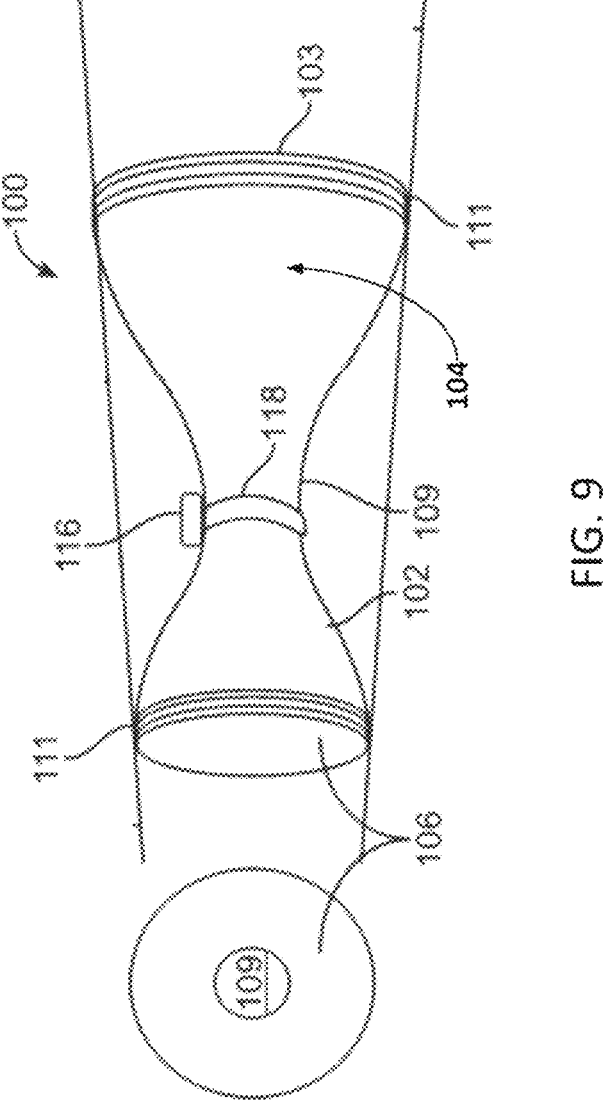
FIG. 9 is a schematic side and end view of the a further alternative embodiment of a vascular flow modulator according to the present disclosure.

In a further alternative embodiment, as shown in FIG. 9, vascular flow restriction device 100 comprises wire mesh body 102 generally as described above with a covering 104. Covering 104 provides both an immediate increase in therapeutic pressure and creates a barrier to unintended thrombus release. In some embodiments, covering 104 comprises a non-porous material such as a silicone coating, or polyurethane coating. In other embodiments, covering 104 may comprise a microporous material such as electro-spun membranes or ePTFE membrane. Pore size for the microporous material should be less than about 10 microns, and in some embodiments less than about 1 micron. In some cases, a more open porous mesh may be desirable, but it is still advantageous to have a pore size that limits release of clinically relevant thrombus, e.g. less than 100 microns. Materials for porous coverings may comprise meshes utilized in embolic filters (e.g. for carotid stenting), thin films with laser/mechanical cut holes or perforations, or woven fabrics with a tight weave pattern providing the desired porosity. Suitable mesh materials may comprise fluoropolymer films, polyurethane films, or weaves of PTFE fibers, PET fibers, etc.

Vascular flow restriction device 100 may be placed substantially in the same manner as described above in connection with device 10 and illustrated, for example, in FIGS. 1-4. When device 100 is implanted at a treatment location in the vasculature, such as the coronary sinus, blood flow velocity and pressure may be modulated. The general hourglass shape of body 102 with central narrowed orifice region 109 may be formed as described above. When released from the delivery catheter, device 100 immediately expands and due to covering 104 captures a volume of blood in the void volume defined annularly around the narrowed orifice region between the covering and vessel wall. Thus, as a result of covering 104, device 100 not only may provide an immediate pressure drop for a therapeutic benefit to the patient, but also may prevent thrombus from the stagnation of blood trapped in the annular volume between the covering and the vessel wall.

Nitinol or other resilient material rings 111 may be provided around the outside of distal opening 103 and proximal opening 106 to allow for collapse and expansion of body 102 for transport through the vasculature to and expansion at the deployment site to match the patient anatomy, including for patients whose coronary sinus reduces in diameter from the opening inward. Resilient rings 111 may be formed, for example, from Nitinol wire or braid and may also serve as anchors for body 102 and may further include anchor features such as barbs or coils, etc. Multiple different sizes may be provided to accommodate different patient sizes and clinical situations. In a further alternative embodiment, flow restriction device 100 may employ a recapture system such as recapture fiber 40 and drawstring 42 as described above may be utilized.

In a further alternative embodiment, electronic package 116 may be optionally provided on an outer surface of body 102, such as in narrowed region 109. Electronic package 116 may include monitoring devices such as pressure or flow sensors that wirelessly communicate with a detection system outside the patient's body to provide information on the patient's hemodynamic anatomy. Electronic package 116 may be optionally included with any of the coronary sinus flow modulator embodiments disclosed herein.

In another alternative, electronic package 116 may be optionally provided to control the diameter of adjustable ring 118 based on pressure measurements or other patient flow metrics. For example, adjustable ring 118 may interface with a micro-motor-driven gear mechanism within electronic package 116 so as to dynamically set the diameter of narrowed section 109 larger or smaller in response to pressure or flow changes as measured by sensors, such as a capacitive pressure sensor, included in the electronic package. An example of an interface between the micro-motor and adjustable ring is a worm or spur-gear drive engaging with a flexible gear rack, such as a "zip-tie" surface, on adjustable ring 118.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure or of the inventions as set forth in following claims.

What is claimed is:

1. A delivery system for a vascular flow restriction implant, comprising:

an inner catheter with a distal end configured for insertion into a patient's vasculature and a proximal end with an inner catheter hub, the inner catheter defining at least one lumen having a side opening on the inner catheter proximally spaced from the distal end, a retractable outer sheath disposed over the inner catheter, said outer sheath having a distal end configured for insertion into the patient's vasculature and a proximal end with an outer sheath hub, wherein relative movement of the outer sheath hub and inner catheter hub exposes or covers the distal end of the inner catheter;

an expandable flow restriction implant received on the distal end of the inner catheter distally with respect to said side opening and inside the outer sheath, wherein the flow restriction implant comprises a self-expanding structure with two open ends; and a recapture fiber extending from the inner catheter hub through the inner catheter lumen and out said side opening to engage the expandable flow restriction device, said recapture fiber manipulable at the inner catheter hub to control expansion or collapse of the flow restriction implant, and wherein the recapture fiber is releasable from the flow restriction implant, wherein the flow restriction implant comprises a drawstring around a proximal end of the flow restriction device configured to collapse said device when tensioned; and the recapture fiber comprises a looped fiber with two opposite ends lying together at a recapture fiber port in the inner catheter hub and a bight end passing through the inner catheter side opening and through the drawstring of the flow restriction implant such that pulling the two opposite ends of the recapture fiber together collapses the flow restriction device and pulling one end removes the recapture fiber.

* * * * *